(12) United States Patent
Raines, Jr.

(10) Patent No.: US 7,731,132 B2
(45) Date of Patent: Jun. 8, 2010

(54) MEDICATION FLUID TUBE STABILIZATION DEVICE

(75) Inventor: Larry Raines, Jr., Hahira, GA (US)

(73) Assignee: Fricker/Raines/Sinnott, LLC, Valdosta, GA (US)

( * ) Notice: Subject to any disclaimer, the term of this patent is extended or adjusted under 35 U.S.C. 154(b) by 0 days.

(21) Appl. No.: 11/513,647

(22) Filed: Aug. 31, 2006

(65) Prior Publication Data

US 2008/0086090 A1 Apr. 10, 2008

(51) Int. Cl.
*F16L 3/22* (2006.01)

(52) U.S. Cl. .............................. 248/68.1; 128/DIG. 26; 128/DIG. 6

(58) Field of Classification Search ......... 604/174–180; 128/DIG. 6, DIG. 26; 248/689, 77, 510, 248/229, 229.16, 74.2, 21.3, 214, 67.7, 68.1, 248/72, 74.1, 74.3
See application file for complete search history.

(56) References Cited

U.S. PATENT DOCUMENTS

| 3,363,864 | A | * | 1/1968 | Olgreen | ...................... | 248/68.1 |
| 4,896,465 | A | | 1/1990 | Rhodes et al. | | |
| 5,016,843 | A | * | 5/1991 | Ward | ........................ | 248/68.1 |
| 5,215,319 | A | | 6/1993 | Farris | | |
| 5,336,179 | A | * | 8/1994 | Ryan | .......................... | 604/80 |
| 5,389,082 | A | * | 2/1995 | Baugues et al. | ............. | 604/174 |
| 5,752,682 | A | | 5/1998 | Anderson | | |
| 6,382,569 | B1 | | 5/2002 | Shattner et al. | | |
| 6,458,104 | B2 | * | 10/2002 | Gautsche | .................... | 604/179 |
| 2001/0049504 | A1 | | 12/2001 | Gautsche et al. | | |
| 2004/0118982 | A1 | | 6/2004 | Shillings et al. | | |
| 2005/0077436 | A1 | | 4/2005 | Nelson | | |
| 2005/0137496 | A1 | * | 6/2005 | Walsh et al. | ................ | 600/561 |
| 2006/0031988 | A1 | | 2/2006 | Morse | | |

FOREIGN PATENT DOCUMENTS

FR 2 641 181 7/1990

* cited by examiner

*Primary Examiner*—Kevin C Sirmons
*Assistant Examiner*—Laura C Schell
(74) *Attorney, Agent, or Firm*—Langdale Vallotton, LLP; John P. Sinnott

(57) ABSTRACT

An interactive fluid tube stabilization device for an intravenous feeding tube is formed of an acrylic material that has a cylindrical shape. A lengthwise slit forms two overlapping sides for the device that can be manually spread apart to fit over and clamp onto the top bed rail of a hospital bed. A flap formed in the side of the device that is opposite to the slit has an arcuate end and a fold line spaced from the end through a distance that is greater than the diameter of the intravenous feeding tube. When the arcuate end is bent toward the top of the bed rail, it forms a gap that accommodates the feeding tube between the device and the flap, enabling most of the drag applied by the feeding tube to be borne by the device and to permit relatively free movement of the tube transverse to the bed rail to accommodate the movement of the patient.

5 Claims, 2 Drawing Sheets

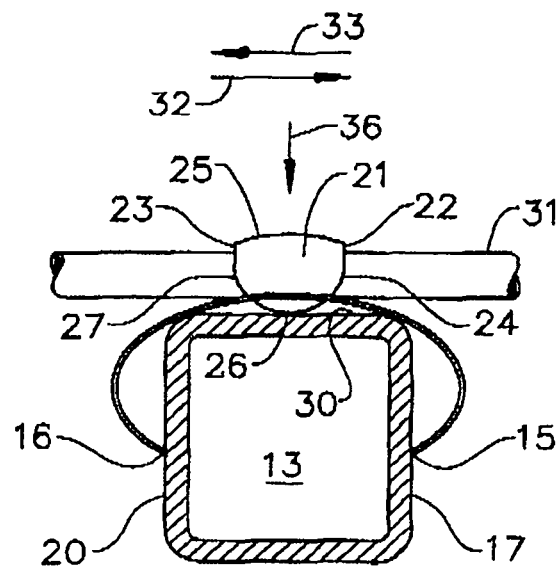
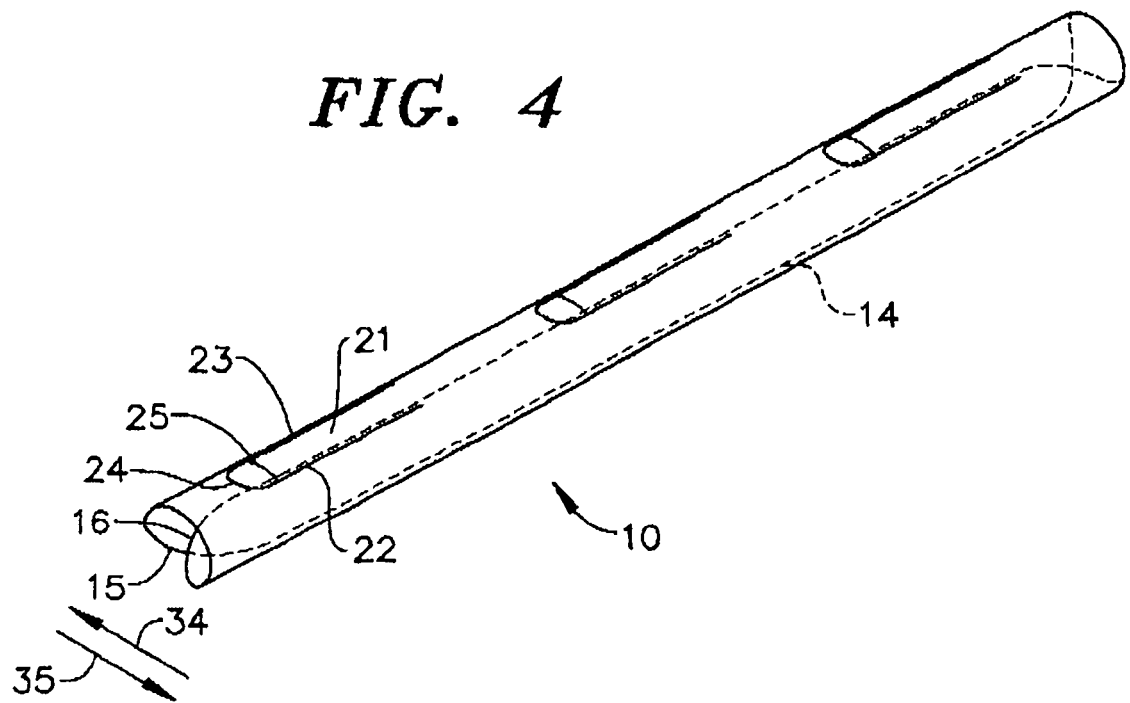

MEDICATION FLUID TUBE STABILIZATION DEVICE

CROSS-REFERENCES TO RELATED APPLICATIONS

None

STATEMENT REGARDING FEDERALLY SPONSORED RESEARCH OF DEVELOPMENT

None

NAMES TO THE PARTIES TO A JOINT RESEARCH AGREEMENT

None

REFERENCE TO "SEQUENCE LISTING"

None

BACKGROUND OF THE INVENTION

This invention relates to devices for stabilizing medication fluid tubes and, more particularly, to an apparatus for supporting a medication fluid tube on a top bed rail in a manner that sustains most of the tube weight and enables the tube to move freely and transversely relative to the bed rail in response to the movement of a patient receiving intravenous medication from the tube, and the like.

Delivering appropriate amounts of fluids intravenously to a patient in a hospital bed is often painful and even can be dangerous for the patient depending on the circumstances. For example, a patient in a hospital bed frequently receives fluids and medications intravenously. This delivery method requires a needle introduced through the patient's skin and penetrating into a vein to be connected to one end of a hollow tube. The other end of the tube is in fluid communication with a source of fluid or liquid medication that is being delivered to the patient. The fluid source, moreover, is secured to a metal stand that raises the source to a level above the patient. In this way, the liquid flows under gravitational force from the source (usually a clear plastic bag) through the tube and any metering device in the tube's passageway into the needle and, ultimately, to the patient. Quite frequently, a single patient will receive several fluids intravenously, requiring a matching number of inserted needles.

To reduce the pain associated with these inserted needles, the portion of each tube next to a respective needle often is bent into a loop of about 180° and, with the needle, is taped to the patient's body. Whenever the patient moves to change position, however, the length and weight of the tubes drag against their attached needles causing considerable pain for the patient. Occasionally, the patient's movement can be extremely painful if one or more of the needles under the weight of the tube tear out of the patient's body.

A further problem can arise from the incorrect identification of a particular tube with its associated fluid source. For example, in situations in which a patient is receiving several intravenous fluids at the same time, the jumble of tubes joining respective intravenous fluid sources to their associated needles can be very confusing, especially to a nurse or nurse's aid working under great pressure and responsible for the care of a number of patients. Consequently, time must be spent sorting out the various tubes for connection to fresh intravenous fluid sources and extreme care must be taken to insure that the proper connections are made.

Controlling the rising cost of medical care and the expensive apparatus that this care requires is a widely known problem. As a result, it also is important that any new and useful medical device should be of a construction that is inexpensive, albeit commensurate with patient safety.

Accordingly, there is a need for an improved, reliable and inexpensive apparatus for relieving the stress applied by intravenous tubes to the needles inserted in a patient in order to reduce the pain caused by these needles as a consequence of the patient's movement. Further in this respect, there also is a need to provide swift and certain identification of the different intravenous fluids associated with the individual tubes through which they are supplied to the patient.

BRIEF SUMMARY OF THE INVENTION

These and other problems that have characterized the prior art are overcome to a large extent through the practice of this invention.

For example, in one illustrative embodiment of the invention, a resilient tube-like device or member has two overlapping sides formed by a lengthwise slit. These overlapping sides are manually spread apart and then pressed over a top bed rail. The inherent resiliency of the device then forces the sides to press against the corresponding sides of the top bed rail and thus to hold the device on the bed rail.

Flaps formed in the device on the side of the device that is opposite to the slit and the overlapping sides can be pried open manually to support loosely one or more fluid tubes between the respective flaps and the adjoining portions of the device that form the flaps. By loosely holding the tubes for free transverse movement relative to the top bed rail, the weight of much of the tube that otherwise would drag against the associated inserted needle is relieved, this weight being borne largely by the top bed rail. The free transverse movement of the tube relative to the top bed rail further relieves the stress applied to the intravenous needle, thereby not only reducing the patient's pain, but also avoiding to a great extent the potential for ripping the needle out of its place of implantation in the patient.

As a salient feature of the invention, the flaps each have a score line spaced from the individual flaps' free ends. These flaps establish respective clearances when their free ends are bent along the score lines toward the top of the bed rail. The clearance so formed between the balance of the flaps and the adjoining portions of the device that form the flaps enable the tube (or tubes) that are seated within the clearances to slip freely in directions that are generally transverse to the direction of the slit and the top bed rail. Thus, the patient on shifting position in the bed will not tear out the needles or even apply undue stresses to the needles at their points of insertion in the patient.

The exposed balance of each of the flaps, moreover, also provides a surface on which the fluid supplied through the tube under the respective flap can be written. In this way, an attendant who must replenish a particular intravenous fluid can identify the correct tube swiftly and accurately.

Thus, there is a provided in accordance with the invention a reliable and inexpensive apparatus for reducing the pain often associated with intravenous fluid delivery. These and other features of the invention will be better understood through the following detailed description of the preferred embodiments of the invention. The scope of the invention, however, is limited only through the claims appended hereto.

BRIEF DESCRIPTION OF THE DRAWING

FIG. 3 is an end view of the embodiment of the invention; and

FIG. 4 is a perspective view of the embodiments of the invention in an unstressed condition.

DETAILED DESCRIPTION OF PREFERRED EMBODIMENTS OF THE INVENTION

Figure 1:
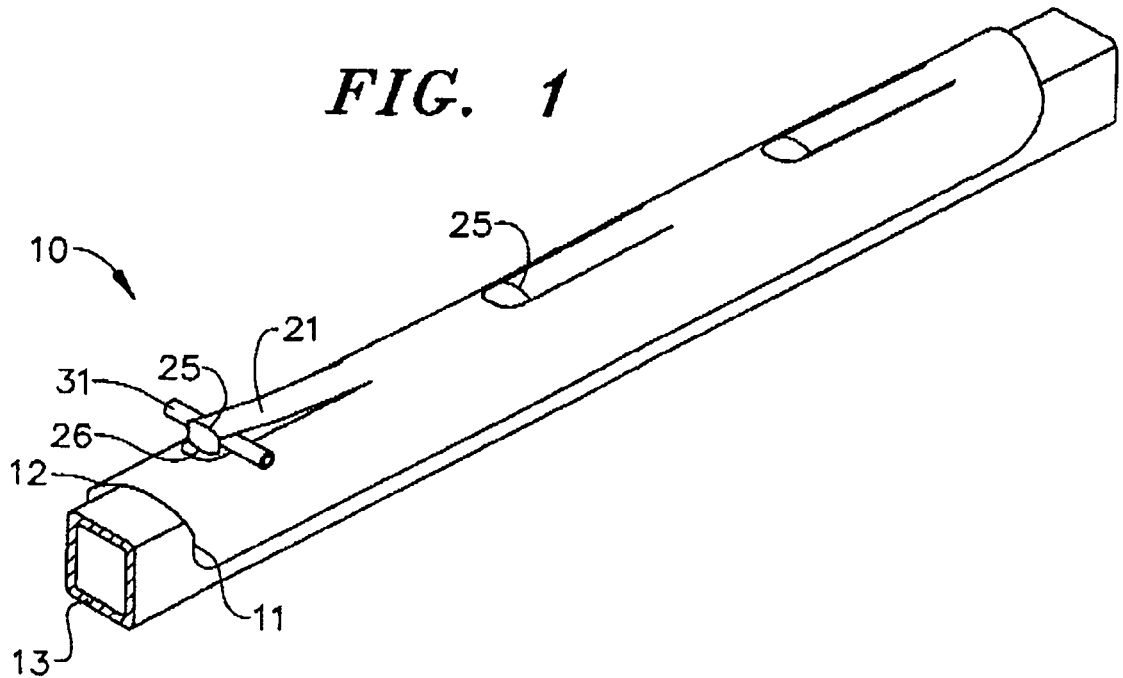
FIG. 1 is a top perspective view of an illustrative embodiment of the invention.

For a more complete appreciation of the invention, attention is invited to FIG. 1 which shows a generally cylindrical member or fluid tube stabilization device 10 in which sides 11, 12 clamp the device 10 to top bed rail 13.

Preferably, the device 10 is formed from a resilient clear plastic tube that enjoys a suitable degree of elasticity. Thus, device 10 shown in FIG. 4 in a relaxed or unstressed state has been provided with a lengthwise slit 14 that forms two overlapping surfaces 15, 16. As described subsequently, the surfaces 15, 16 can be manually spread apart and pressed over the bed rail 13 as shown in FIG. 3 to bear against and engage corresponding portions 17, 20 of the top bed rail 13. As shown, the inherent resiliency of the device applies sufficient frictional force through the now separated surfaces 15, 16 to the corresponding portions 17, 20 of the bed rail 13 to clamp or retain the device 10 firmly in engagement with the bed rail 13 through the stresses that are applied in use to the device 10.

Turning once more to FIG. 4 and in accordance with a salient feature of the invention, a flap 21 is formed in the device 10 by die cutting, or the like, on the side that is generally opposite to the overlapping surfaces 15, 16. The flap 21 has two parallel cuts 22, 23 that each terminate at their corresponding ends through a further arcuate cut 24. Thus, the flap 21 remains joined to the device 10 at the corresponding ends of the cuts 22, 23 that are opposite to the arcuate cut 24.

A further salient feature of the invention is the provision of a score or fold line at the base of the arcuate cut 24. As best illustrated in FIG. 3, the distance between the fold line 25 and tip or end 26 of the arcuate cut 24 when the arcuate cut 24 is bent toward the top bed rail 13 is such that a gap 27 is formed between the fold line 25 and top 30 of the bed rail 13. This gap is sufficiently deep to enable intravenous tube 31 to move freely in directions generally transverse to the bed rail 13 as shown by arrows 32, 33.

Figure 2:
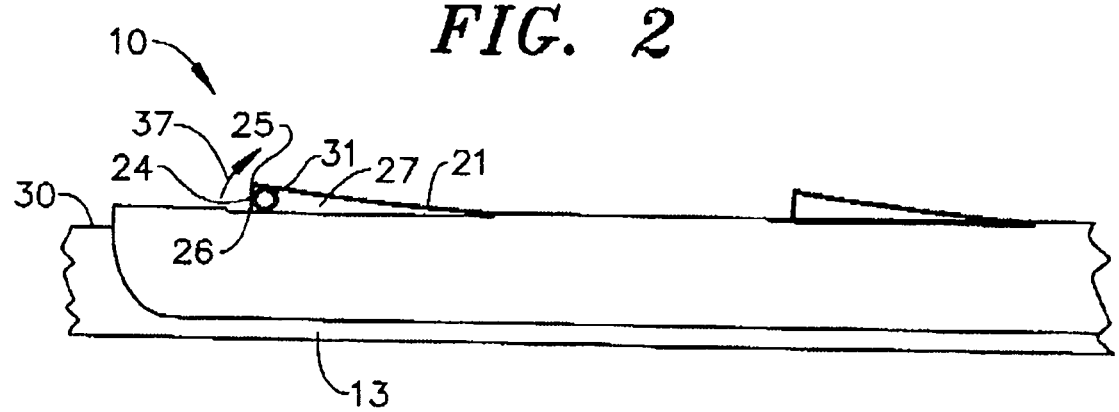
FIG. 2 is a side elevation of the embodiment of the invention shown in FIG. 1.

In operation, to assemble the device 10 shown in FIG. 4, the overlapping surfaces 15, 16 of the device 10 are manually spread apart by pressing the surfaces 15, 16 away from each other in the respective directions of arrows 34, 35. The gap thus formed between the surfaces 15, 16 is sufficiently wide to permit the device 10 to be pressed over the top bed rail 13 in the direction of arrow 36 (FIG. 3). In this manner, the device 10, as shown in FIG. 2, is seated firmly on the top bed rail 13 along the entire length of the device 10.

To accommodate the intravenous tube 31, the flap 21 is manually drawn out of its relaxed seated position in the device 10 in the direction of arrow 37. The intravenous tube 31 is slipped into the portion of the gap 27 that is thus formed between the flap 21 and the adjacent corresponding sides of the device 10. Turning once more to FIG. 3, the arcuate cut 24 is bent under finger pressure at the fold line 25 to enable the tip of the arcuate cut 26 to rest against the top 30 of the top bed rail 13.

Consequently, as shown in FIG. 1, the stress or drag caused by the portion of the intravenous tube 31 between the source of the intravenous fluid (not shown in the drawing) and the device 10 is largely borne by the device 10 and is not applied directly to the intravenous needles inserted in the patient. As the patient moves, moreover, the intravenous tube 31 is capable of generally free movement through the portion of the gap 27 that is formed between the flap 21 and the adjacent portions of the device 10 in directions that are generally transverse to the top bed rail 13. In this way, the stress applied to the intravenous needle (not shown in the drawing) is further reduced and largely eliminates the possibility that movement by the patient would otherwise tear out the implanted intravenous needle. Further in this respect, the tip 26 of the arcuate cut 24 need not bear directly against the bed rail top 30, it being sufficient for the purpose of the invention that the length of the arcuate cut 24 from the fold line 25 to the tip 26 is greater than the diameter of the intravenous tube 31 in order to retain the tube 31 between the arcuate cut 24, the balance of the flap 21 and the corresponding sides of the device 10 that are adjacent to the parallel cuts 22, 23 that form the flap 21.

Further with respect to the invention, the nature of the intravenous fluid supported by the device 10, illustrated in FIG. 1, can be written directly on the associated flap 21. As a result, time spent sorting out and the potential for error in identifying the correct tube among several in a group of intravenous solutions being applied to the patent is also reduced. Additionally, the device 10 also provides space for advertising pharmaceuticals and the like.

What is claimed is:

1. A stabilization device for intravenous tubes for selective attachment to a lengthwise bedrail comprising an inherently resilient and arcuate member having a lengthwise opening forming two sides to said member each for clamping a respective portion of the bedrail there between, more than one flap, each of said flaps having an end thereof formed in said member and a bend in each of said flaps spacing each flap from said opening, means having lengths formed in each of said flap ends, said flap ends means being generally transverse to said opening and the lengthwise bedrail and spaced from said respective flap ends a distance for enabling at least a portion of the drag of at least one of the intravenous tubes to be borne by the bedrail and to move freely and transversely relative to the bedrail.

2. A stabilization device according to claim 1 in which said inherently resilient and arcuate member comprise said two sides thereof that overlap.

3. A stabilization device according to claim 1 wherein each of said flap end means further comprise shapes, said shapes having respective tips thereof to bear against the bedrail to form gaps between said flap ends means and surfaces on said arcuate member adjacent to said respective flap ends means to establish portions of said gaps that are generally equal to the diameters of the intravenous tubes.

4. A stabilization device according to claim 1 in which said member further comprises an acrylic plastic.

5. A stabilization device according to claim 1 wherein said flap ends means comprise distances from said respective flap ends greater than the diameters of the intravenous tubes to enable said respective flap ends means to bear against the bedrail.

* * * * *